(12) United States Patent
Kularatne

(10) Patent No.: US 11,986,540 B2
(45) Date of Patent: May 21, 2024

(54) COMPOSITIONS INCLUDING PAFOLACIANINE FOR THE IDENTIFICATION OF MALIGNANT LESIONS

(71) Applicant: ON TARGET LABORATORIES, LLC., West Lafayette, IN (US)

(72) Inventor: Sumith A. Kularatne, West Lafayette, IN (US)

(73) Assignee: ON TARGET LABORATORIES, LLC, West Lafayette, IN (US)

( * ) Notice: Subject to any disclaimer, the term of this patent is extended or adjusted under 35 U.S.C. 154(b) by 0 days.

Patent file contains an affidavit/declaration under 37 CFR 1.130(b).

(21) Appl. No.: 18/111,704

(22) Filed: Feb. 20, 2023

(65) Prior Publication Data

US 2023/0263911 A1 Aug. 24, 2023

Related U.S. Application Data

(60) Provisional application No. 63/312,965, filed on Feb. 23, 2022.

(51) Int. Cl.
| | |
|---|---|
| *A61B 5/00* | (2006.01) |
| *A61B 8/00* | (2006.01) |
| *A61B 10/00* | (2006.01) |
| *A61K 49/00* | (2006.01) |
| *A61P 35/00* | (2006.01) |

(52) U.S. Cl.
CPC ........ *A61K 49/0032* (2013.01); *A61B 5/0071* (2013.01); *A61P 35/00* (2018.01)

(58) Field of Classification Search
CPC ............ A61K 49/0032; A61K 49/0052; A61K 49/006; A61B 5/0071; A61P 35/00
See application file for complete search history.

(56) References Cited

U.S. PATENT DOCUMENTS

| | | | |
|---|---|---|---|
| 9,061,057 B2 * | 6/2015 | Kularatne | G01N 33/6893 |
| 9,233,175 B2 * | 1/2016 | Low | A61K 49/0032 |
| 9,254,341 B2 * | 2/2016 | Kularatne | G01N 33/56966 |
| 9,333,270 B2 * | 5/2016 | Low | G01N 33/582 |
| 9,341,629 B2 * | 5/2016 | Kularatne | A61P 37/00 |
| 9,782,497 B2 * | 10/2017 | Kularatne | A61K 49/0032 |
| 9,789,208 B2 * | 10/2017 | Kularatne | A61K 49/0032 |
| 10,881,747 B2 * | 1/2021 | Kularatne | G01N 33/582 |
| 2010/0322854 A1 | 12/2010 | Low et al. | |
| 2014/0271476 A1 | 9/2014 | Kularatne et al. | |
| 2014/0275533 A1 | 9/2014 | Kularatne et al. | |

OTHER PUBLICATIONS

Cytalux™ Nov. 2021.*
Randall et al. (Gynecol. Oncol. 2019, 155, 63-68).*
Thabet et al. (J. Vasc. Interv. Radiol. 2014, 25, 1922-1927).*
Predina et al. (Annals Surg 2017, 266, 479-488).*
PTC, "International Search Report," regarding Application No. PCT/US23/13479, 18 pages, dated Jun. 26, 2023.

* cited by examiner

*Primary Examiner* — Michael G. Hartley
*Assistant Examiner* — Melissa J Perreira
(74) *Attorney, Agent, or Firm* — McAndrews, Held & Malloy, Ltd.

(57) ABSTRACT

A composition is configured to be administered to a subject undergoing a malignant lesion resection procedure. The composition comprises a pharmaceutically effective amount of pafolacianine or a pharmaceutically acceptable salt thereof. The pafolacianine or a pharmaceutically acceptable salt thereof is configured to bind one or more malignant lesions and emit an optical signal.

15 Claims, 5 Drawing Sheets

COMPOSITIONS INCLUDING PAFOLACIANINE FOR THE IDENTIFICATION OF MALIGNANT LESIONS

RELATED APPLICATIONS

The present patent application claims the priority benefit of U.S. Provisional Patent Application Ser. No. 63/312,965, filed Feb. 23, 2022, the content of which is hereby incorporated by reference in its entirety into this disclosure.

BACKGROUND

Many treatment plans for cancer, such as ovarian and lung cancer, for example, include surgery. For example, a patient with cancer may undergo surgery with the goal of removing the cancerous cells. In some aspects, a method or system to help the surgeon visualize the malignant lesions that are intended to be removed via surgery may be used. In some such cases, an imaging agent may be provided to the patient and a light source or imaging technique may be used to capture the imaging agent within the patient's body. For example, a patient may receive the imaging agent via ingestion, intravenous injection, topically, or another way. Such visualization techniques may result in better surgical outcomes (e.g., a higher percentage of cancerous cells removed) in comparison to surgeries that do not use visualization techniques.

Although conventional visualization compositions, methods, and techniques may provide better visualization of cancerous lesions within the body of a patient than surgeries that do not use any visualization composition, method, or technique, such conventional compositions, methods, and techniques may not be entirely effective in identifying cancerous portions of the body. Thus, there is a need for a composition and method that is more effective in identifying cancerous lesions in a patient's body.

Embodiments of the invention address these challenges and other challenges, individually and collectively.

Further limitations and disadvantages of conventional and traditional approaches will become apparent to one of skill in the art, through comparison of such systems with some aspects of the present disclosure as set forth in the remainder of the present application with reference to the drawings.

SUMMARY

The inventors have recognized the need for improved visualization techniques and compositions for identifying cancerous lesions in a body of a patient. Thus, the compositions, methods, and techniques described herein may enable visualization of cancerous tumors, cells, and/or lesions that conventional compositions and techniques would not otherwise identify.

The present technology, it is believed, targets folate receptors (FR) which may be overexpressed in certain cancer cells (e.g., ovarian and lung cancer cells). The disclosed compositions, methods, and techniques include pafolacianine that is believed to bind to FR-expressing cancer cells and fluoresce when exposed to light to allow for visualization of the FR-expressing cancer cells bound to the pafolacianine. The present technology may improve detection and specificity of said detection of cancer cells.

In one aspect, a composition configured to be administered to a subject undergoing a malignant lesion resection procedure, the composition comprising a pharmaceutically effective amount of pafolacianine, wherein the pafolacianine is configured to fluoresce to identify one or more malignant lesions.

In some aspects, the one or more of the malignant lesions comprise ovarian cancer. In other aspects, the one or more of the malignant lesions comprise lung cancer. In yet other aspects, the pharmaceutically effective amount of pafolacianine comprises at least about 0.025 mg of pafolacianine per about 1 kg body weight of the subject. In further aspects, the composition is configured to be administered to the subject intravenously.

In some aspects, the composition comprises an injectable solution. In other aspects, the solution is bluish green. In other aspects, the solution is transparent or translucent. In yet other aspects, the composition comprises between about 1 mg and about 20 mg of pafolacianine per about 1.6 mL volume of solution. In further aspects, the composition comprises about 3.2 mg pafolacianine per about 1.6 mL volume of solution.

In some aspects, the about 3.2 mg of pafolacianine per about 1.6 mL volume of solution is equivalent to about 3.4 mg of pafolacianine sodium per about 1.6 mL volume of solution. In other aspects, the pafolacianine sodium has the following chemical structure:

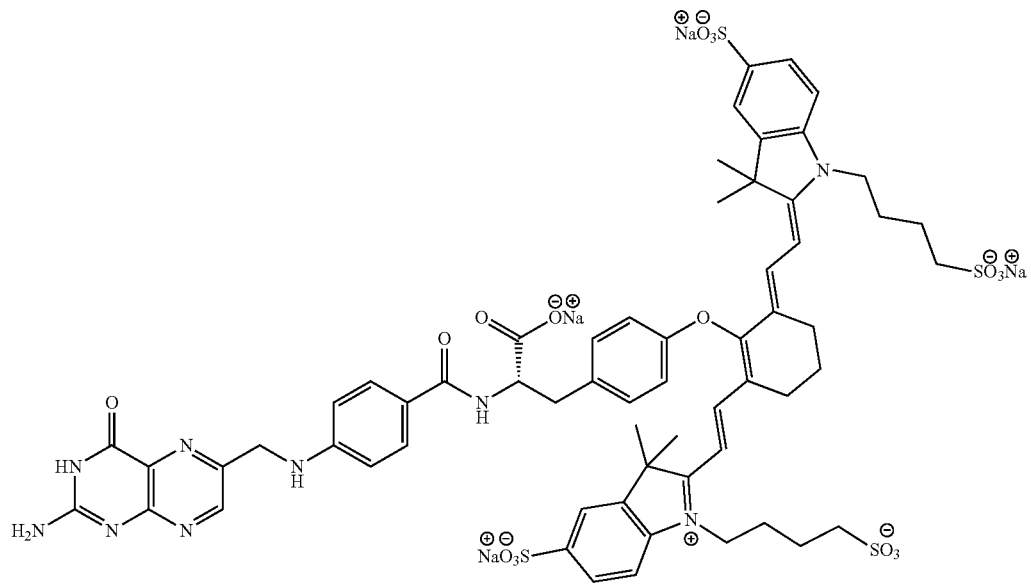

In some aspects, the composition comprises at least one of sodium chloride, potassium phosphate monobasic, or sodium phosphate dibasic heptahydrate. In other aspects, the composition comprises between about 1 mg and about 50 mg sodium chloride per about 1.6 mL volume of solution. In yet other aspects, the composition comprises about 14.4 mg sodium chloride per about 1.6 mL volume of solution. In further aspects, the composition comprises between about 0.01 mg and about 5 mg potassium phosphate monobasic per about 1.6 mL volume of solution.

In some aspects, the composition comprises about 0.23 mg potassium phosphate monobasic per about 1.6 mL volume of solution. In other aspects, the composition comprises between about 0.1 mg and about 10 mg sodium phosphate dibasic heptahydrate per about 1.6 mL volume of solution. In yet other aspects, the composition comprises about 1.27 mg sodium phosphate dibasic heptahydrate per about 1.6 mL volume of solution. In further aspects, the composition comprises about 3.2 mg of pafolacianine, about 14.4 mg sodium chloride, about 0.23 mg potassium phosphate monobasic, and about 1.27 mg sodium phosphate dibasic heptahydrate per about 1.6 mL volume of solution.

In some aspects, the pH of the composition is between about 6 and about 8. In other aspects, the composition comprises at least one of sodium hydroxide or hydrochloric acid. In yet other aspects, at least one of sodium hydroxide or hydrochloric acid is used to adjust the pH of the composition. In further aspects, a solution comprising the composition is diluted prior to administering the composition to the subject.

In some aspects, the solution is diluted with a 5% dextrose solution. In other aspects, the solution is diluted with about 220 mL to about 250 mL of the 5% dextrose solution. In yet other aspects, the composition is configured to be administered to the subject about 1 to about 24 hours prior to the malignant lesion resection procedure. In further aspects, the composition is configured to be administered to the subject over a period of time.

In some aspects, the period of time comprises about 1 to about 3 hours. In other aspects, the pafolacianine fluoresces upon exposure to light in the near-infrared range. In yet other aspects, the pafolacianine fluoresces upon exposure to light with a wavelength between about 760 nm and about 785 nm. In further aspects, the pafolacianine emits fluorescence between about 790 nm and about 815 nm.

In some aspects, the composition is contained in a vial. In other aspects, the vial is a single-dose vial. In yet other aspects, a carton comprises at least 10 vials. In further aspects, the at least 10 vials are individually wrapped.

In some aspects, the subject is an animal. In other aspects, the subject is a mammal. In yet other aspects, the subject is a human. In further aspects, the subject is an adult.

In one aspect, a method of treating a subject undergoing a malignant lesion resection procedure comprises administering a pharmaceutically effective amount of a composition comprising pafolacianine to the subject; and causing the pafolacianine to fluoresce.

In some aspects, the method comprises identifying, based on the fluorescence of the pafolacianine, one or more malignant lesions. In other aspects, the method comprises resecting one or more of the malignant lesions. In yet other aspects, the one or more of the malignant lesions comprise ovarian cancer. In further aspects, the one or more of the malignant lesions comprise lung cancer.

In some aspects, the pharmaceutically effective amount comprises at least about 0.025 mg of pafolacianine per about 1 kg body weight of the subject. In other aspects, the composition is administered to the subject intravenously. In yet other aspects, the composition comprises an injectable solution. In further aspects, the solution is bluish green.

In some aspects, the solution is transparent or translucent. In other aspects, the solution comprises between about 1 mg and about 20 mg of pafolacianine per about 1.6 mL volume of solution. In yet other aspects, the composition comprises about 3.2 mg pafolacianine per about 1.6 mL volume of solution. In further aspects, the about 3.2 mg of pafolacianine per about 1.6 mL volume of solution is equivalent to about 3.4 mg of pafolacianine sodium per about 1.6 mL volume of solution.

In some aspects, the pafolacianine sodium has the following chemical structure:

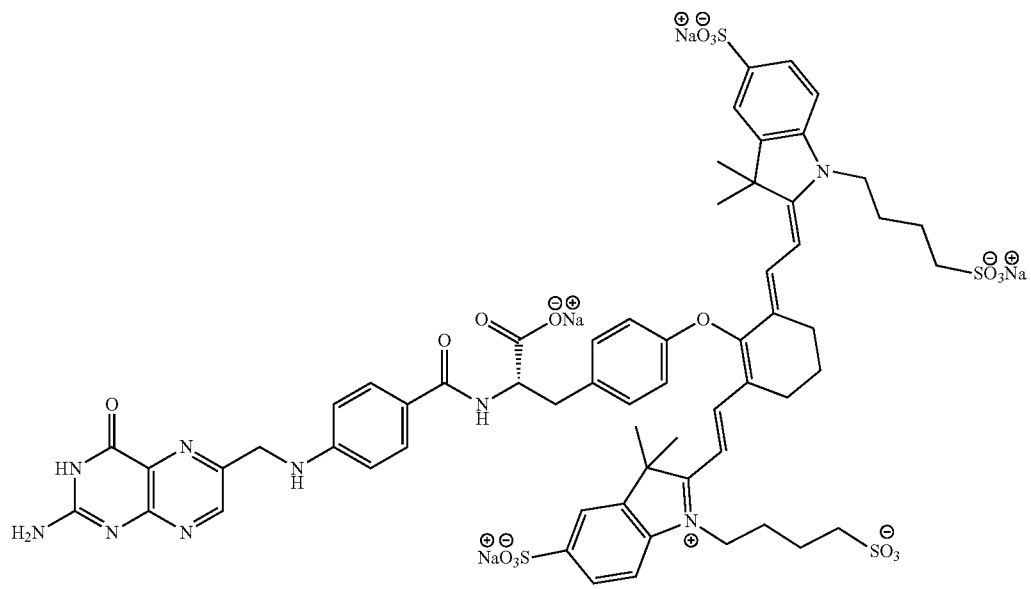

In some aspects, the solution further comprises at least one of sodium chloride, potassium phosphate monobasic, or sodium phosphate dibasic heptahydrate. In other aspects, the solution comprises between about 1 mg and about 50 mg sodium chloride per about 1.6 mL volume of solution. In yet other aspects, the solution comprises about 14.4 mg sodium chloride per about 1.6 mL volume of solution. In further aspects, the solution comprises between about 0.01 mg and about 5 mg potassium phosphate monobasic per about 1.6 mL volume of solution.

In some aspects, the solution comprises about 0.23 mg potassium phosphate monobasic per about 1.6 mL volume of solution. In other aspects, the solution comprises between about 0.1 mg and about 10 mg sodium phosphate dibasic heptahydrate per about 1.6 mL volume of solution. In yet other aspects, the solution comprises about 1.27 mg sodium phosphate dibasic heptahydrate per about 1.6 mL volume of solution. In further aspects, the solution comprises about 3.2 mg of pafolacianine, about 14.4 mg sodium chloride, about 0.23 mg potassium phosphate monobasic, and about 1.27 mg sodium phosphate dibasic heptahydrate per about 1.6 mL volume of solution.

In some aspects, the pH of the solution is between about 6 and about 8. In other aspects, the solution further comprises at least one of sodium hydroxide or hydrochloric acid. In yet other aspects, the at least one of sodium hydroxide or hydrochloric acid is used to adjust the pH of the solution. In further aspects, the method comprises diluting the solution prior to administering the composition to the subject.

In some aspects, diluting the solution comprises diluting the solution with a 5% dextrose solution. In other aspects, diluting the solution comprises diluting the solution with about 220 mL to about 250 mL of the 5% dextrose solution. In yet other aspects, administering the pharmaceutically effective amount of the composition comprises administering the pharmaceutically effective amount of the composition about 1 to about 24 hours prior to the malignant lesion resection procedure. In further aspects, administering the pharmaceutically effective amount of the composition comprises administering the pharmaceutically effective amount of the composition over a period of time.

In some aspects, the period of time comprises about 1 to about 3 hours. In other aspects, causing the pafolacianine to fluoresce comprises exposing the pafolacianine to light in the near-infrared range. In yet other aspects, causing the pafolacianine to fluoresce comprises exposing the pafolacianine to light with a wavelength between about 760 nm and about 785 nm. In further aspects, the pafolacianine emits fluorescence between about 790 nm and about 815 nm.

In some aspects, the composition is contained in a vial. In other aspects, the vial is a single-dose vial. In yet other aspects, a carton comprises 10 vials. In further aspects, the 10 vials are individually wrapped.

In some aspects, the subject is an animal. In other aspects, the subject is a mammal. In yet other aspects, the subject is a human. In further examples, the subject is an adult.

In some aspects, the fluorescence of the pafolacianine is detected using an imaging system or imaging software. In another aspect, the imaging system or imaging software is selected from the group consisting of imaging system FAST (fiber-optic array scanning technology), flow cytometry, confocal microscopy, two-photon microscopy, epifluorescence microscopic, florescence microscopic methods, fluorescence goggle, and an innovative wearable. In some aspect, the fluorescence of the pafolacianine is detected in vivo.

In some aspects, the method further comprises guiding a flexible probe to the malignant lesion after administration of the composition comprising pafolacianine. In some aspects, the flexible probe is a flexible endoscope, fluorescence endoscopic imaging probe, fiber scope, video scope, gastroscope, colonoscope, bronchoscope, laryngoscope, cystoscope, duodenoscope, enteroscope, ureteroscope, sigmoidoscope, enteroscope, choleodoscope, rhinolaryngoscope, angioscope, or hysteroscope. In other aspects, the flexible probe is equipped to detect wavelengths that have an absorption and emission maxima between about 400 nm and about 900 nm.

In some aspects, the resection procedure is performed using iBiopsy, iKnife, iLaser, iBurner, an electric cutting loop, a rotating blade, a curved blade, an expandable blade, dissectors with cutting blades, blunt dissectors, pinchers, an electrolyzable element, a biopsy needle, microwave ablation probe, radiofrequency ablation probe, cryo-ablation probe, or laser.

In some aspects, the resection procedure is non-invasive.

In some aspects, the resection procedure is performed manually or using robotic-assisted technology.

DETAILED DESCRIPTION

Figure 1:
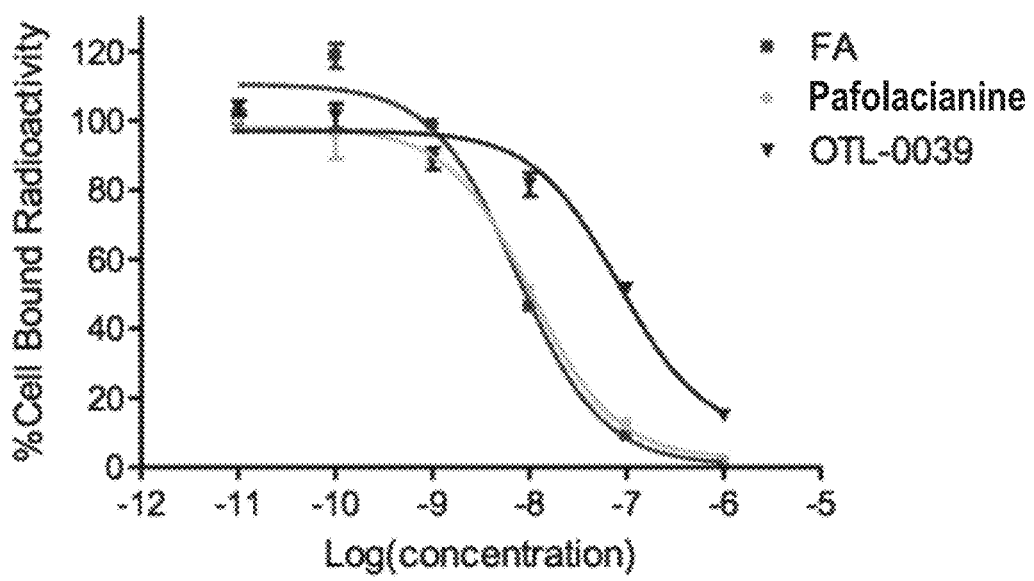
FIG. 1 is a graph illustrating the relative binding of pafolacianine, the L-isomer of pafolacianine (OTL0039), and folic acid to FRs.

The present technology provides compositions comprising pafolacianine and methods of using such compositions, such as, for example, methods of identifying or visualizing cancerous cells in a body of a patient.

As used herein, the following conventional unit abbreviations and terms are used as follows: "pg" refers to picogram, "ng" refers to nanogram, "µg" refers to microgram, "mg" refers to milligram, "g" refers to gram, "kg" refers to kilogram, "mL" refers to milliliter, "h" refers to hour and "t" refers to time.

As used herein, "patient" and/or "subject" refers to a human or an animal. In some aspects, the human is an adult. In other aspects, the human may be a child. In some aspects, the animal is mammal. In other aspects, the animal is an animal other than a mammal. "Patient" and "subject" are used interchangeably throughout the disclosure.

As used herein, "pharmaceutically effective amount" refers to an effective dose or effective concentration that produces a biological response.

As utilized herein, "and/or" means any one or more of the items in the list joined by "and/or". As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z".

The term "exemplary" means serving as a non-limiting example, instance, or illustration. As utilized herein, the terms "e.g.," and "for example" set off lists of one or more non-limiting examples, instances, or illustrations.

As used herein, the words "about" and "approximately," when used to modify or describe a value (or range of values), mean reasonably close to that value or range of values (e.g., +/−10% of the value or range of values). Thus, the aspects described herein are not limited to only the recited values and ranges of values, but rather should include reasonably workable deviations.

In the present specification, use of the singular includes the plural except where specifically indicated.

As mentioned above, a malignant lesion resection procedure, or surgical removal of cancerous cells or other malignant diseases, is a part of many treatment plans for such cancers or malignant diseases. In some cases, surgical removal may be one of the most effective methods of treating cancer. For example, resection of all detectable malignant lesions may result in no detectable return of the disease in approximately 50% of all cancer patients. In cases in which the disease does return, the malignant lesion resection procedure may still extend the life expectancy or reduce morbidity of the patient. Thus, for the malignant lesion resection procedure to have the best possible outcome, it is important that as many of the cancerous cells are removed during surgery as possible.

In many cases, a visualization method is used to identify malignant lesions. Conventional visualization methods include identification based on a color, texture, and/or morphology of a tumor. Additionally, or alternatively, a tumor may be identified based on a difference in plasticity, elasticity, or solidity from adjacent healthy tissues. In some aspects, these such methods may be performed by a surgeon without the use of additional tools or compositions, or with the tools and compositions typically used during the surgical procedure. For example, a surgeon may use their own senses to identify the malignant lesions based on color, texture, morphology, plasticity, elasticity, and/or solidity. Another example conventional visualization technique is the use of a fluorescent dye that may flow passively from the tumor into draining lymph nodes. Such conventional dyes may fluorescence in the visible light range. The fluorescent lymph nodes (e.g., due to the dye) can then be visually identified and resected in order to determine if the cancerous cells have metastasized to the lymph nodes. However, in many cases, at least a portion of the malignant lesions may not be identified, and therefore not resected, with use of these conventional visualization methods. Moreover, some conventional dyes may auto-fluoresce in the visible light range, have a relatively short shelf life, be relatively unstable, and have poor tissue permeability.

Thus, there is a need for improved visualization techniques and compositions to better identify malignant lesions in a body of a patient. Disclosed are compositions, formulations, and methods for identification of cancerous cells. The compositions, formulations, and methods disclosed include pafolacianine. Without being bound by theory, it is believed that pafolacianine has an increased binding affinity to folate receptor (FR) positive cancers. The compositions and formulations including pafolacianine bind to such FRs of the malignant lesions expressing the FR, which in turn, can be used to identify the malignant lesions. Such compositions, formulations, and methods may result in increased visualization and identification of malignant lesions expressing FRs in comparison to the conventional visualization methods discussed above. In this way, use of the compositions, formulations, and methods disclosed herein may result in improved outcomes for cancer patients (e.g., a resection of a higher percentage of malignant lesions, increased life expectancy, a better chance of remission of the cancer, and/or reduced mortality). Additionally, the disclosed technology may have reduced auto-fluorescence, increased shelf life, increased stability, and/or more efficient tissue permeability in comparison to conventional dyes.

As discussed above, the compositions, formulations, and methods include pafolacianine that is thought to have an increased binding affinity to FRs. In this way, the compositions and methods disclosed may result in improved visualization of cancerous lesions in cancers that express or over-express FRs. Such cancers include, for example, ovarian cancer, kidney cancer, lung cancer, endometrium cancer, breast cancer, and colon cancer. Other cancers not specifically disclosed herein may also express or over-express FRs. In such cases, the compositions, formulations, and methods disclosed herein may result in improved identification of those cancers as well. The use of the compositions, formulations, and methods disclosed herein are contemplated for any type of cancer or other malignant disease.

Thus, the present disclosure allows identification of a biological tissue that expresses a FR by contacting the tissue with a composition comprising pafolacianine of the present disclosure and allowing time for the composition to distribute within the tissue and interact with the site of FR. After a sufficient time for such interaction has passed, the tissue is illuminated with an excitation light to cause the composition to fluoresce. The fluorescence is then observed to visualize malignant lesions. In like manner, the compositions of the present disclosure are used to identify a target cell type in a biological sample by contacting the biological sample with such compositions for a time and under conditions that allow for binding of the composition to at least one cell of the target cell type. The bound composition is then caused to fluorescence to enable identification of the tissue to which the composition is bound to.

The compositions disclosed herein include an optical imaging agent. In some aspects, the optical imaging agent is pafolacianine. In some aspects, the compositions include pafolacianine as a pharmaceutically acceptable salt. In some aspects, the compositions include pafolacianine as a tetrasodium salt. For example, the composition may include pafolacianine sodium. Pafolacianine sodium has a chemical formula of (S)-2-(4-(((2-amino-4-oxo-3,4-dihydropteridin-6-yl)methyl)amino)benzamido)-3-(4-(((E)-2-((E)-2-(3,3-dimethyl-5-sulfonato-1-(4-sulfonatobutyl)-3H-indol-1-ium-2-yl)vinyl)-6-((E)-2-(3,3-dimethyl-5-sulfonato-1-(4-sulfonatobutyl)indolin-2-ylidene)ethylidene)cyclohex-1-en-1-1) oxy)phenyl)propanoate hydrate tetrasodium and a molar mass of 1414.42 g/mol. The general structure of pafolacianine sodium of the present technology is:

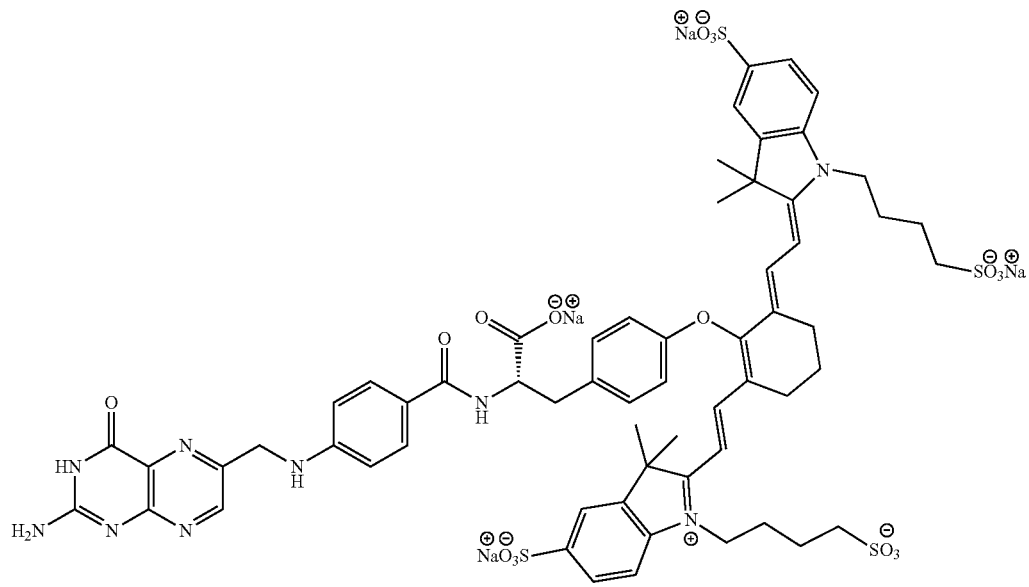

Without intending to be bound by theory, it is believed that pafolacianine binds to FR-expressing cancer cells. In some aspects, pafolacianine may bind to FR-expressing cancer cells with at least about a 1 nanomolar (nM) affinity, at least about a 0.75 nM affinity, at least about a 0.5 nanomolar (nM) affinity, at least about a 0.25 nanomolar (nM) affinity, at least about a 0.1 nanomolar (nM) affinity, at least about a 0.05 nanomolar (nM) affinity, at least about a 0.01 nanomolar (nM) affinity, or at least about a 0.001 nanomolar (nM) affinity. Pafolacianine may then internalize in the cancer cells via receptor-mediated endocytosis, therefore concentrating in FR-positive cancer tissues.

Once absorbed in the tissues, the compositions of the present disclosure can be used to identify the cancer cells by fluorescing the pafolacianine. Pafolacianine is excited using light with at least one excitation wavelength in the near-infrared range (e.g., between about 600 nm and about 1000 nm). In some aspects, pafolacianine absorbs light in the near-infrared range from about 600 nm to about 900 nm, from about 700 nm to about 900 nm, from about 700 nm to about 800 nm, from about 750 nm to about 800 nm, or from about 760 nm to about 785 nm. In some aspects, peak absorption by pafolacianine may occur at about 776 nm. In some aspects, pafolacianine emits fluorescence between about 600 nm to about 900 nm, from about 700 nm to about 900 nm, from about 700 nm to about 850 nm, from about 750 nm to about 850 nm, or from about 790 nm to about 815 nm. In some aspects, peak emission by pafolacianine may occur at about 796 nm. Fluorescence by the pafolacianine bound to FR of cancer cells may enable visualization of said cancer cells. In some aspects, visualization using pafolacianine may be improved (e.g., identify more cancerous cells) than conventional visualization methods. Moreover, due to the use of near-infrared light instead of light in the visual range, the compositions and formulations discussed herein may be more stable, have a longer shelf life, result in less auto-fluorescence, and better permeate tissue than conventional dyes.

In some aspects, operating rooms for surgical procedures may be equipped with an overhead light that produces wavelengths of light in the range discussed above. For example, an operating room may include at least one lamp that produces light in the appropriate wavelength. In this way, the at least one lamp producing light in the appropriate wavelength can be directed into a body cavity, surgical opening, or the like in order to cause the pafolacianine bound to the cancerous cells to fluorescence. In some aspects, the surgeon (or other professional) may be able to observe the fluorescence directly, without requiring additional tools, accessories, or special equipment, to identify the malignant lesions. In other examples, additional tools, accessories, or special equipment may additionally, or alternatively, be used to visualize the fluorescence of the pafolacianine and identify the malignant lesions. For example, an endoscopic device may be used to deliver the excitation light to the site, to receive fluorescence emanating from the site, and/or to aid in formation of an image of the fluorescence from the malignant lesion. Additionally, or alternatively, in some aspects, an image processing device, such as, for example, a CCD camera, a display, a photon collecting device, or the like may be used to help visualize the cancerous cells.

The compositions and formulations disclosed herein can be administered by any route known to those of skill in the art, such as, for example, intravenously, topically, intraarticularly, intracisternally, intraocularly, intraventricularly, intrathecally, intramuscularly, intraperitoneally, intradermally, intratracheally, or intracavitarily. In some aspects, the most suitable route for administration may vary depending upon the disease state to be treated, or the location of the suspected condition or tumor to be identified.

In some aspects, the disclosed compositions may be administered intravenously. For example, pafolacianine may be administered intravenously as a solution. The solution may contain an effective amount (e.g., a quantity of the pafolacianine that enables identification of malignant lesions in the body of the patient) of pafolacianine and any other compositions, ingredients, agents, solvents, buffers, preservatives, antioxidants, diluents, or the like.

The composition may be administered before the surgery begins, before an incision is made during the surgery procedure, after the surgery as begun, after the surgical cavity and site of the tumor has been revealed by the surgery, or any other suitable time. In some aspects, the composition may be administered intravenously to a patient at least about one hour before initiation of fluorescence imaging. For example, the pafolacianine may be administered between about 1 hour and about 24 hours prior to surgery, about 1 hour and about 12 hours prior to surgery, about 1 hour and about 9 hours prior to surgery, between about 1 hour and about 7 hours prior to surgery, between about 1 hour and about 5 hours prior to surgery, between about 1 hour and about 3 hours prior to surgery, or between about 1 hour and 2 hours prior to surgery. In some such examples, providing at least 1 hour prior to surgery may enable the composition to sufficiently bind to the FR-expressing cancer cells to allow for fluorescence and therefore visualization of the cancer cells. In other aspects, the composition may be provided to the patient less than about 1 hour prior to surgery.

In some aspects, the pafolacianine composition may be provided to the patient (e.g., intravenously) over a period of time. For example, in some aspects, the pafolacianine may be administered to the patient over a period of about 1 hour or more. In some such aspects, the composition may be administered to the patient using an infusion line over a period of about 1 hour, about 1.5 hours, about 2 hours, or 3 about hours. For example, the composition may be administered to the patient over a period between about 1 hour and about 3 hours. In other aspects, the composition may be administered over a different period of time.

In some aspects, the compositions disclosed herein may include an amount of pafolacianine from about 0.5 mg or higher, from about 2.5 mg or higher, from about 5.0 mg or higher, from about 7.5 mg or higher, from about 10 mg or higher, from about 20 mg or higher, from about 30 mg or higher, from about 40 mg or higher, from about 50 mg or higher, from about 60 mg or higher, from about 70 mg or higher, from about 80 mg or higher, from about 90 mg or higher, or from about 100 mg or higher, and include any additional increments thereof, for example, 0.1, 0.2, 0.25, 0.3, 0.4, 0.5, 0.6, 0.7, 0.75, 0.8, 0.9 or 1.0 mg and multiplied factors thereof (e.g., ×1, ×2, ×2.5, ×5, ×10, ×100, or the like). In some aspects, the formulations include between about 1 mg and about 20 mg, between about 1 mg and about 10 mg, between about 1 mg and about 5 mg, between about 1 mg and about 4 mg, or between about 2 mg and about 4 mg. For example, some formulations may include about 3.2 mg of pafolacianine. In aspects in which the formulation includes pafolacianine sodium, the formulation may include between about 1 mg and about 20 mg, between about 1 mg and about 10 mg, between about 1 mg and about 5 mg, between about 1 mg and about 4 mg, between about 2 mg and about 4 mg, or about 3.4 mg of pafolacianine sodium.

Pafolacianine may be administered to the patient in any suitable dose. In some aspects, suitable dosages of pafolacianine include, but are not limited to between about 0.01 mg and about 1 mg per 1 kg bodyweight of the patient, between about 0.01 mg and about 0.5 mg per 1 kg bodyweight of the patient, between about 0.01 mg and about 0.25 mg per 1 kg bodyweight of the patient, between about 0.01 mg and about 0.1 mg per 1 kg bodyweight of the patient, between about 0.01 mg and about 0.09 mg per 1 kg bodyweight of the patient, between about 0.01 mg and about 0.07 mg per 1 kg bodyweight of the patient, between about 0.025 mg and about 0.07 mg per 1 kg bodyweight of the patient, or between about 0.025 mg and about 0.05 mg per 1 kg bodyweight of the patient. In some aspects, about 0.025 mg of pafolacianine may be administered per 1 kg bodyweight of the patient. In other aspects, a different amount of pafolacianine may be administered per 1 kg bodyweight of the patient. Similar doses of compositions containing pafolacianine sodium may be administered to the patient.

In some aspects, the present technology provides a combination formulation including pafolacianine and at least one other composition, ingredient, agent, solvent, buffer, preservative, antioxidant, diluent, or the like. For example, the at least one other composition, ingredient, agent, solvent, buffer, preservative, antioxidant, or diluent may be a salt. In some such aspects, the salt may include sodium chloride, potassium phosphate monobasic, sodium phosphate dibasic heptahydrate, sodium bisulfate, calcium chloride, potassium iodide, or another salt. As one non-limiting aspect, a combination formulation may include pafolacianine (and/or pafolacianine sodium), sodium chloride, potassium phosphate monobasic, and sodium phosphate dibasic heptahydrate. In some aspects, the combination formulation may additionally, or alternatively, include an acid, a base, and/or a buffer. For example, in some such aspects, the combination formulation may include sodium hydroxide, hydrochloric acid, perchloric acid, hydroiodic acid, nitric acid, sulfuric acid, potassium hydroxide, and/or calcium hydroxide. As one non-limiting aspect, a combination formulation may include sodium hydroxide, and/or hydrochloric acid.

As another non-limiting example, a combination formulation may include pafolacianine (and/or pafolacianine sodium), sodium chloride, potassium phosphate monobasic, sodium phosphate dibasic heptahydrate, sodium hydroxide, and/or hydrochloric acid. In some aspects, the combination formulation may include between about 1 mg and about 50 mg, between about 1 mg and about 25 mg, between about 1 mg and about 20 mg, between about 1 mg and about 15 mg, between about 5 mg and about 50 mg, between about 5 mg and about 25 mg, between about 5 mg and about 20 mg, between about 5 mg and about 15 mg, between about 10 mg and about 15 mg, or about 14.4 mg sodium chloride. In some aspects, the combination formulation may include between about 0.01 mg and about 5 mg, between about 0.01 mg and about 1 mg, between about 0.01 mg and about 0.5 mg, between about 0.01 mg and about 0.25 mg, between about 0.05 mg and about 5 mg, between about 0.05 mg and about 1 mg, between about 0.05 mg and about 0.5 mg, between about 0.05 mg and about 0.25 mg, between about 0.1 mg and about 0.25 mg, or about 0.23 mg potassium phosphate monobasic. In some aspects, the combination formulation may include between 0.1 mg and about 10 mg, about 0.1 mg and about 5 mg, between about 0.1 mg and about 2.5 mg, between about 0.5 mg and about 10 mg, between about 0.5 mg and about 5 mg, between about 0.5 mg and about 2.5 mg, between about 1 mg and about 10 mg, between about 1 mg and about 5 mg, between about 1 mg and about 2.5 mg, or about 1.27 mg potassium phosphate monobasic. In some such aspects, the combination formulation may include about 3.2 mg pafolacianine (equivalent to about 3.4 mg of pafolacianine sodium), 14.4 mg sodium chloride, 0.23 potassium phosphate monobasic, 1.27 mg sodium phosphate dibasic heptahydrate in about 1.6 mL volume of solution. Thus, in some aspects, 3.2 mg of pafolacianine (equivalent to about 3.4 mg of pafolacianine sodium) per about 1.6 mL volume of solution of the combination formula may be administered to the patient. In other aspects, the combination formulation may include additional or alternative compositions, ingredients, agents, solvents, buffers, preservatives, antioxidants, diluents, or the like. Moreover, in other aspects, the combination formulation may include different quantities of any of the compositions, ingredients, agents, solvents, buffers, preservatives, antioxidants, diluents, or the like.

In some aspects, the pH of the composition may be between about 6 and about 9, between about 6 and about 8, between about 7 and about 8, or between about 7.1 and about 7.8. In other aspects, the pH may be different. In some aspects, a buffer or another composition may be used to adjust the pH of the formulation to between about 6 and about 9, between about 6 and about 8, between about 7 and about 8, or between about 7.1 and about 7.8. For example, the pH of the composition formulation may be adjusted using sodium hydroxide and/or hydrochloric acid. In other aspects, the pH may be adjusted using a different buffer, composition, substance, or solvent, such as, for example, perchloric acid, hydroiodic acid, nitric acid, sulfuric acid, potassium hydroxide, and/or calcium hydroxide.

In some aspects, the dosages discussed above may be supplied in a single-dose vial. For example, a single-dose vial may include 3.2 mg of pafolacianine (or 3.4 mg of pafolacianine sodium) in about 1.6 mL of the combination formula solution described above. In other aspects, the formulation may include between about 1 mg and about 20 mg, between about 1 mg and about 10 mg, between about 1 mg and about 5 mg, between about 1 mg and about 4 mg, or between about 2 mg and about 4 mg of pafolacianine or between about 1 mg and about 10 mg, between about 1 mg and about 5 mg, between about 1 mg and about 4 mg, between about 2 mg and about 4 mg, or about 3.4 mg of pafolacianine sodium. Such a combination formulation may be a dark, bluish green, transparent, aqueous solution. In other aspects, the dosages may not be supplied in single-dose vials. In such aspects, the vials (or other packaging) may include any suitable number of doses, such as, for example, about 20 doses, about 10 doses, about 5 doses, or about 2 doses. In some aspects, a vial may be a sealed, amber, glass vial. In some aspects, the vials may be individually packaged and supplied in a carton containing at least about 5 vials, at least about 10 vials, at least about 20 vials, at least about 50 vials, or at least about 100 vials. In other aspects, the composition may come in an alternative form, have different quantities, be packaged differently, and/or have a different appearance.

In some aspects, the compositions disclosed herein may be diluted prior to administration to the patient. For example, the pafolacianine may be diluted in a dextrose solution, such as, for example, a 5% dextrose solution. In some such aspects, about 0.025 mg of pafolacianine per 1 kg of the bodyweight of the patient may be diluted in about 220 mL to about 250 mL of a 5% dextrose solution. In other examples, additional or alternative solutions and/or concentrations of solutions may be used to dilute the disclosed compositions.

The presently described technology and its advantages will be better understood by reference to the following examples. These examples are provided to describe specific aspects of the present technology. By providing these specific examples, it is not intended limit the scope and spirit of the present technology. It will be understood by those skilled in the art that the full scope of the presently described technology encompasses the subject matter defined by the claims appending this specification, and any alterations, modifications, or equivalents of those claims.

EXAMPLES

Example 1: Detection of Malignant Lesions with Compositions Including Pafolacianine The safety and efficacy of the compositions disclosed herein was evaluated in a randomized, multicenter, open-label study. The study enrolled 178 women diagnosed with ovarian cancer or with high clinical suspicion of ovarian cancer scheduled to undergo primary surgical cytoreduction, interval debulking, or recurrent ovarian cancer surgery. One hundred and fifty women highly suspicious for or with confirmed ovarian cancer received a composition including pafolacianine (dosed at 0.025 mg/kg at least 1 hour before initiation of fluorescence imaging). Among them, 134 women with mean age 60 (range 33 to 81) years received both normal light imaging evaluation and fluorescence imaging evaluation (the Intent-to-Image set).

The study assessed the proportion of patients with at least one evaluable ovarian cancer lesion confirmed by central pathology that was detected with compositions including pafolacianine under fluorescent light but not under normal light or palpation and not otherwise identified for resection prior to surgery. The detection proportion was estimated in women who underwent both normal light and fluorescent light (Intent-to-Image Set), see Table 1.

TABLE 1

| | (N = 134)<br>Patients with at least one confirmed<br>ovarian cancer evaluable lesion |
|---|---|
| Number (n) | 36 |
| Proportion (%) | 0.269 (26.9%) |
| 95% Confidence Interval (proportion) | (0.196*, 0.352) |

Patient-level false positive rate of compositions including pafolacianine with near-infrared fluorescent light with respect to the detection of ovarian cancer lesions confirmed by central pathology was 20.2% with 95% confidence interval (13.7%, 28.0%).

Example 2: Pharmacodynamics

Tumor to background ratios were studied with different mass doses of pafolacianine. High tumor to background ratio was observed with a dose of 0.025 mg pafolacianine per 1 kg of bodyweight of a patient.

Example 3: In Vitro Pharmacodynamics

KB cells (a derivative of HeLa cells) that over-express FR were combined with [3H]-folic acid in the presence of increasing concentrations (0.1 nM-1 µM) of pafolacianine (L-isomer), OTL0039 (D-isomer) or folic acid. Pafolacianine demonstrated a high affinity for FR (KD=10.4 nM), which compared well with the binding affinity of folic acid (KD=7.4 nM) as shown in FIG. 1. In contrast, the D-isomer of pafolacianine (OTL0039) exhibited relatively lower affinity for the receptor (KD=81.8 nM). Pafolacianine competed well with [3H]-folic acid for the receptor.

Example 4: In Vivo Pharmacodynamics

Figure 2A:
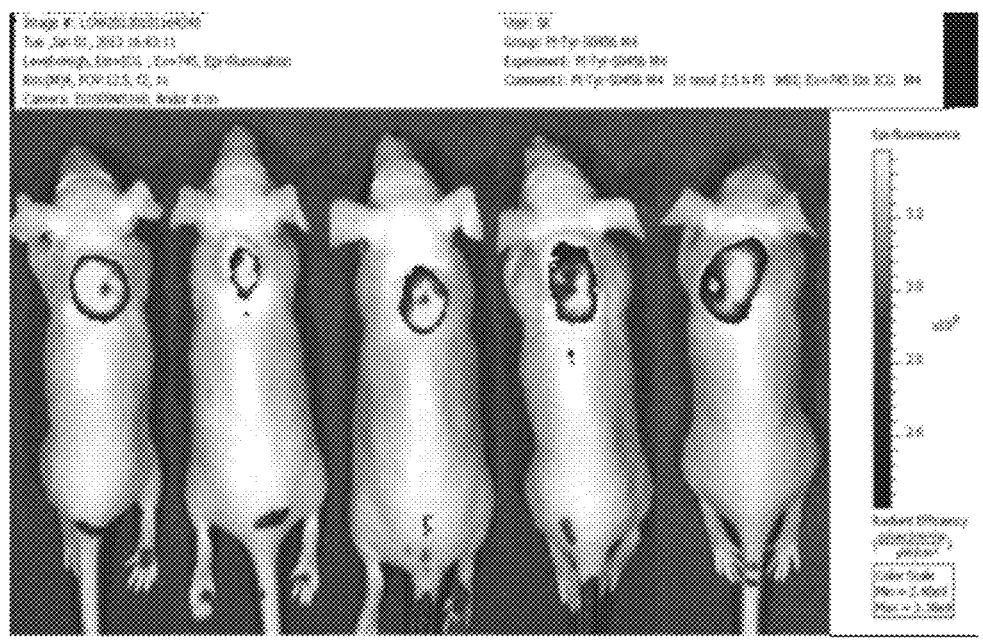
FIG. 2A is a whole body fluorescence image of FR-positive KB tumor-bearing mice injected with pafolacianine.
Figure 2B:
FIG. 2B is a whole body fluorescence image of FR-positive KB tumor-bearing mice injected with the L-isomer of pafolacianine (OTL0039).
Figure 2C:
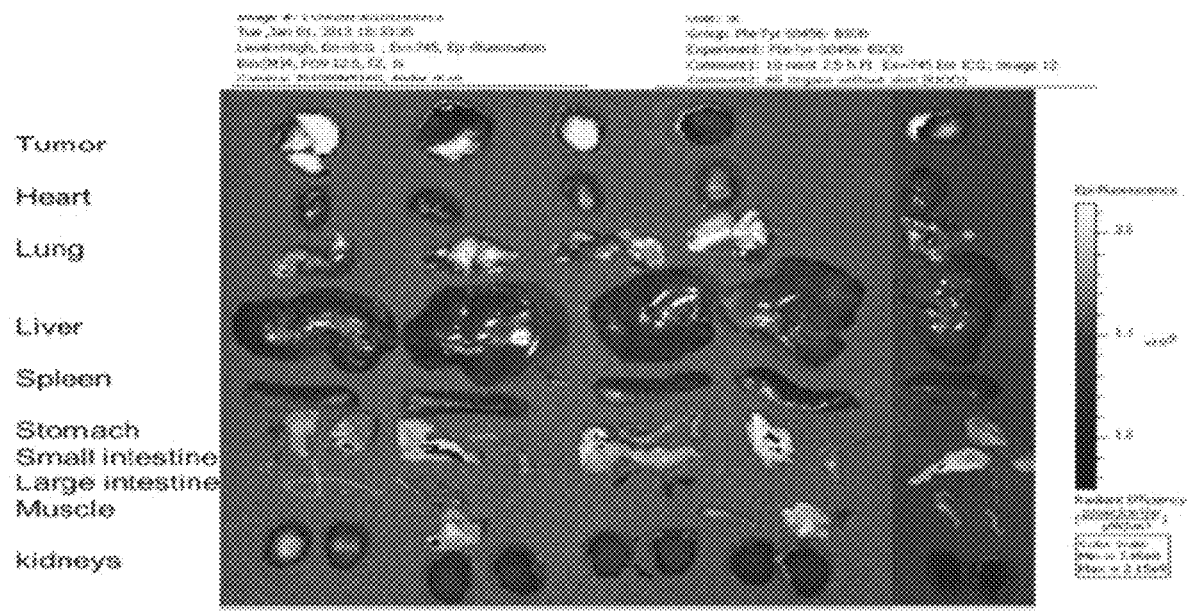
FIG. 2C is a fluorescence image of tissue distribution 2.5 hours post injection with pafolacianine.
Figure 2D:
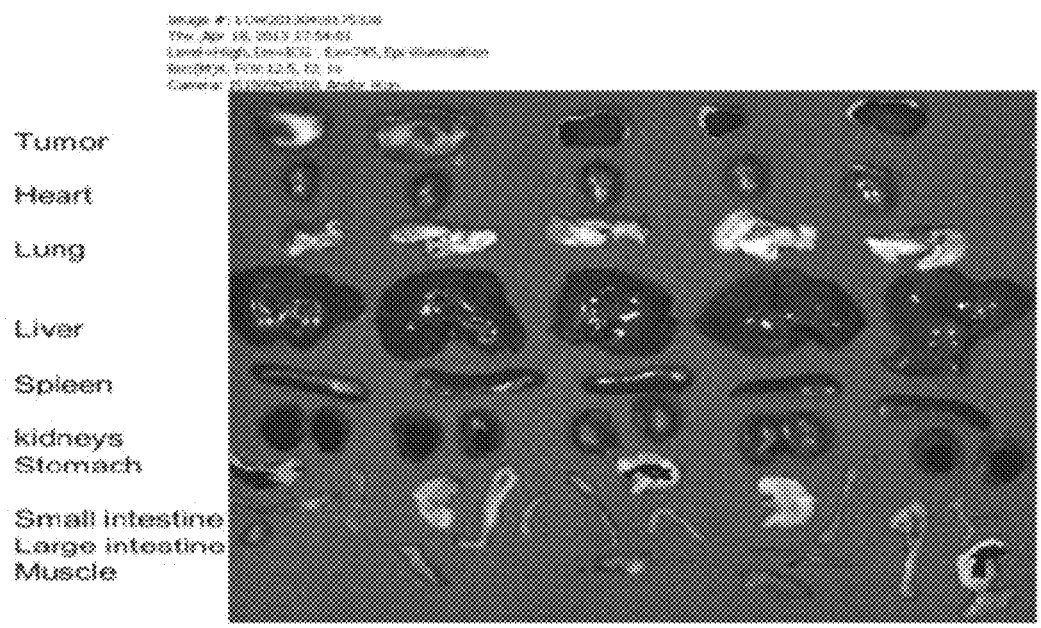
FIG. 2D is a fluorescence image of tissue distribution 2.5 hours post injection with the L-isomer of pafolacianine (OTL0039).

Whole body imaging and tissue distribution of pafolacianine and OTL0039 was performed in female nu/nu mice bearing FR-positive KB cell tumor xenografts. Results showed fluorescence primarily in the tumors 2.5 hours after intravenous (IV) administration of 10 nmol pafolacianine, with fluorescence signal also observed in the kidneys (FIGS. 2A and 2C). Uptake of pafolacianine in the kidneys was anticipated, since the apical membrane of the proximal tubule of the kidney has been demonstrated to express high levels of FR. All other normal tissues displayed little or no fluorescence signal, resulting in excellent tumor-to-normal tissue fluorescence ratios. The tissue distribution pattern of OTL0039 (FIG. 2D) was similar to that of pafolacianine (FIG. 2C), although with a weaker fluorescence signal intensity than pafolacianine in both the tumors (FIG. 2B) and kidneys. This observation was consistent with the lower binding affinity of the D-isomer for FR compared with the L-isomer. Tumor fluorescence was brighter in mice receiving pafolacianine compared with other folate-conjugated near infrared dyes such as LS288, IR800 and ZW800.

Figures 3A, 3B:
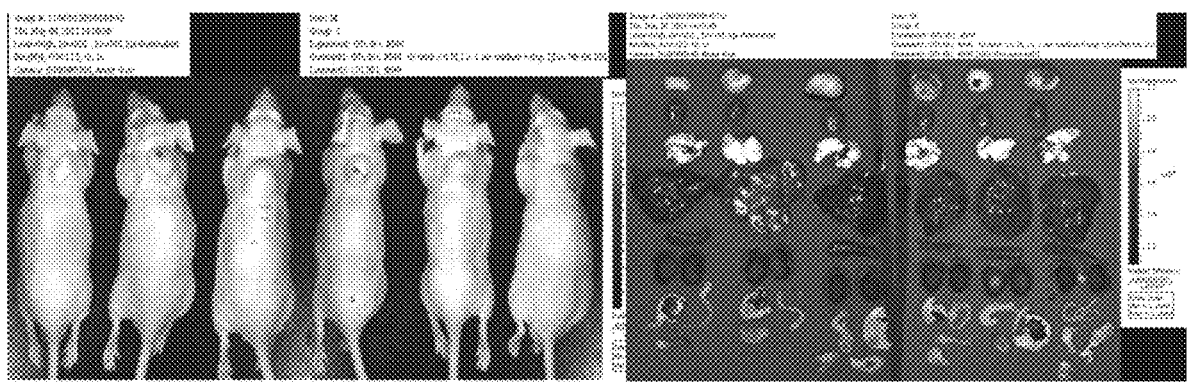
FIG. 3A is a whole body fluorescence image of FR-negative A549 tumor-bearing mice injected with pafolacianine.
FIG. 3B is a fluorescence image of tissue distribution from the FR-negative A549 tumor-bearing mice injected with pafolacianine of FIG. 3A.

The optimal dose range for pafolacianine with respect to tumor-to-background ratio in FR-positive tumor-bearing mice was 1 to 30 nmol/mouse, with lower fluorescence intensity observed in tumors at a lower dose (0.3 nmol) and higher fluorescence intensity observed in other tissues at doses above 30 nmol. In a second experiment, pafolacianine whole body imaging and tissue distribution was examined again; however, this experiment was performed in female nu/nu mice bearing FR-negative A549 cell tumor xenografts. In this study, fluorescence was primarily noted in kidneys, with no fluorescence observed in the FR-negative tumors (FIG. 3). Thus, pafolacianine did not target FR-negative tumors in vivo, demonstrating specificity of the imaging agent for FR-positive tumors.

Example 5: Secondary Pharmacodynamics

Pafolacianine (5 μM) was evaluated in an in vitro ligand binding screen (ExpresSProfile; Cerep 100010238), which assessed the potential for pafolacianine "off-target" binding to a broad panel of 55 pharmacologically-relevant receptors, ion channels and transporters. The results from the binding experiments showed that the positive values for % specific binding of pafolacianine ranged between 0.2 and 29.7% and the negative values ranged between −0.3% and −16.8%. These data suggest no significant affinity of pafolacianine to a comprehensive set of off-target proteins and support the specificity of pafolacianine for FR binding.

Example 6: Pharmacokinetics

The mean maximum plasma concentration ($C_{max}$) of pafolacianine is 59.1±5.94 ng/mL and the area under the plasma concentration-time curve to infinity ($AUC_{inf}$) is 63.6±12.6 ng·hr/mL.

Elimination

The elimination half-life of pafolacianine is 0.44±0.23 hours and mean plasma clearance is 28.6±4.97 L/hr.

Metabolism

Pafolacianine sodium is not metabolized by cytochrome P450 (CYP) enzymes.

Excretion

Following a single IV infusion of radiolabeled pafolacianine sodium, approximately 35% of the dose was recovered in urine (19.1%) and in feces (15.8%) after approximately 3-5 weeks.

Specific Populations

No clinically significant differences in pharmacokinetics of pafolacianine were identified based on age 18-89 years, weight 41.6-133.6 kg, mild to moderate renal impairment (creatine clearance (CLcr) 30 to 89 mL/min), or mild to moderate hepatic impairment (total bilirubin<3 upper limit of normal (ULN) and aspartate transaminase (AST)>ULN).

Absorption

Figure 4:
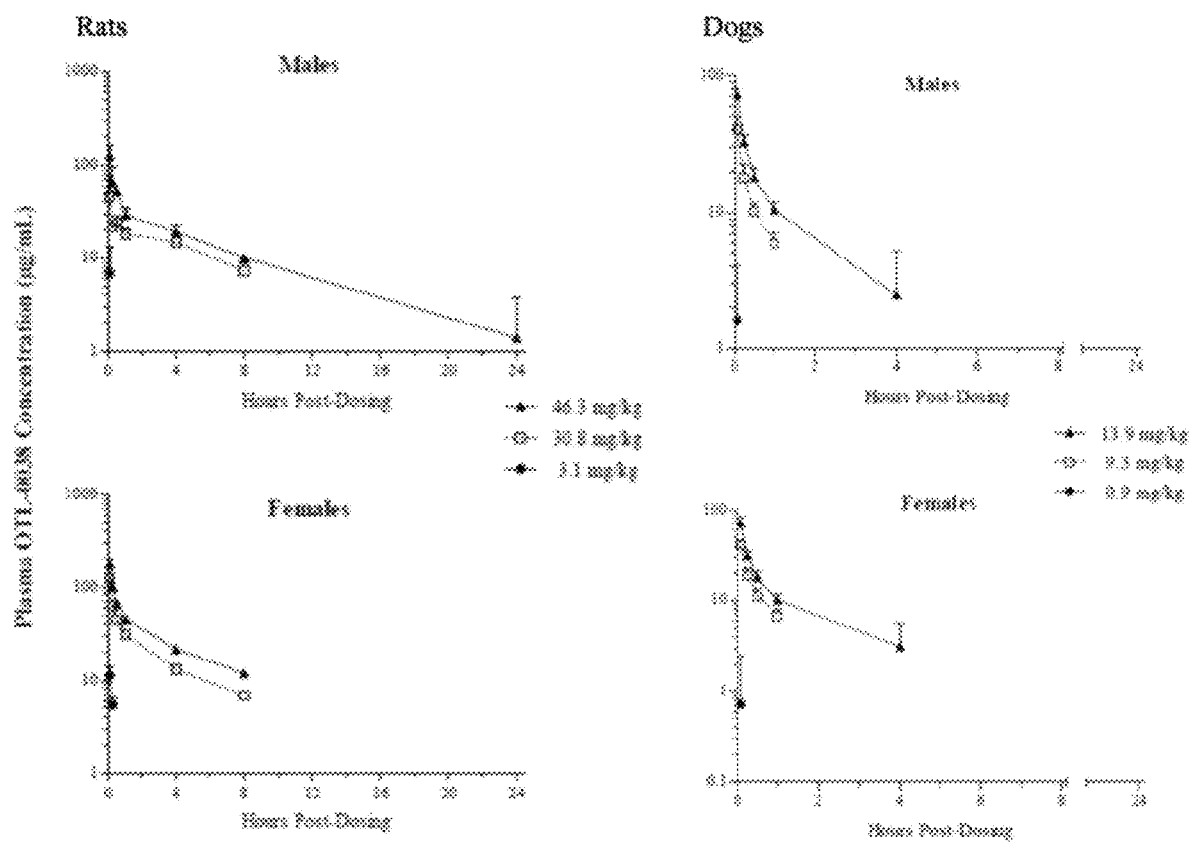
FIG. 4 are graphs illustrating the mean concentrations of pafolacianine in male and female rats and dogs after intravenous administration of pafolacianine.

Following a single IV administration of pafolacianine to male and female rats, systemic exposure (AUClast) to pafolacianine appeared similar between males and females at the 46.3 mg/kg dose levels (Table 2). There was a slight trend for higher AUClast values in females versus males at the two lower dose levels; however, due to sparse sampling of blood, the significance of this slight trend could not be evaluated. Values for AUClast were calculated, but the time associated with the last measurable concentration was variable (Tlast; 5 min to 24 hr), which confounded the ability to assess dose proportionality. Terminal data were generally sparse and/or the terminal phase was not sufficiently defined (FIG. 4). Thus, parameters dependent on accurate determination of the terminal phase (AUCinf, T1/2, CL, Vz) were not reported.

Following a single IV administration of pafolacianine to male and female dogs, systemic exposure (C0, AUClast) to pafolacianine appeared similar between males and females at all dose levels (Table 3). Similar to rats, dog AUClast values were calculated from a range of concentration-time data with Tlast values varying from 5 minutes to 4 hours. In addition, there were limited dogs with reportable TK at 0.9 mg/kg (N=1-2). As a consequence, dose proportionality was not assessed for dogs. Terminal data were generally sparse (i.e., 2 or fewer measurable concentrations in the terminal phase, (FIG. 4). Similar to rat, parameters dependent on accurate determination of the terminal phase (AUCinf, T1/2, CL, Vz) were not reported.

TABLE 2

| Sex: | Males | | | Females | | |
|---|---|---|---|---|---|---|
| Dose (mg/kg) | 3.1 | 30.8 | 46.3 | 3.1 | 30.8 | 46.3 |
| Parameter (Units) | | | Study Day 0 | | | |
| $AUC_{last}$ (μg · h/mL) | 0.570 | 119 | 286 | 2.53 | 166 | 255 |
| DN $AUC_{last}$ (μg · h/mL)/ (mg/kg) | 0.184 | 3.86 | 6.18 | 0.816 | 5.39 | 5.51 |
| $AUC_{inf}$ (μg · h/mL) | NC | NR* | NR* | NC | NR* | NR* |
| $C_0$ (μg/mL) | 6.87 | 65.7 | 174 | 16.2 | 178 | 231 |

DN = Dose normalized.
*Extent of extrapolation failed to meet acceptance criteria.
NC = Not calculable; NR: not reported.

TABLE 3

| Sex: | Males | | | Females | | |
|---|---|---|---|---|---|---|
| Dose (mg/kg) | 0.9 | 9.3 | 13.9 | 0.9 | 9.3 | 13.9 |
| Parameter (Units) | | | Study Day 0 | | | |
| $AUC_{last}$ (μg · h/mL) | 0.397 (N = 2) | 16.8 (3.00) | 42.1 (16.1) | 0.362 (N = 1) | 17.6 (2.30) | 44.0 (14.0) |
| DN $AUC_{last}$ (μg · h/mL)/(mg/kg) | 0.442 (N = 2) | 1.81 (0.324) | 3.03 (1.16) | 0.402 (N = 1) | 1.89 (0.249) | 3.17 (1.01) |
| $AUC_{inf}$ (μg · h/mL) | NC | NR | NR | NC | NR | NR |
| $C_0$ (μg/mL) | 3.79 (N = 2) | 58.5 (17.4) | 107 (14.2) | 4.36 (N = 1) | 61.5 (11.3) | 109 (21.4) |

SD: standard deviation;
DN = Dose normalized;
NR = Not reported (extent of extrapolation failed to meet acceptance criteria);
NC = Not calculable Repeat Dosing Male and female rats received a once-weekly IV dose of pafolacianine (0.9, 9.3 and 13.9 mg/kg) for 14 days. TK parameters are summarized in Table 4. On both Day 1 and Day 13, increases in pafolacianine exposure (AUCinf) were trending slightly greater than dose proportional, noting that sparse blood sampling was employed so the variability in the AUCs could not be assessed. After a 14.9-fold increase in dose, AUCinf increased ~18-fold on Day 1 and ~20-fold on Day 13 (genders combined). There were no apparent gender-related differences, and no accumulation or changes in TK parameters were evident after repeated once-weekly dosing for 3 weeks. CL was slow (relative to hepatic blood flow) and Vss was moderate. Mean T1/2 ranged from approximately 6 to 11 hours.

TABLE 4

| Parameter/Dose | 3.1 mg/kg | | 30.8 mg/kg | | 46.3 mg/kg | |
|---|---|---|---|---|---|---|
| (mg/kg) | M | F | M | F | M | F |
| Day 0 | | | | | | |
| $AUC_{inf}$ (µg · h/mL) | 19.2 | 19.1 | 235 | 237 | 342 | 361 |
| DN $AUC_{inf}$ (µg · h/mL)/(mg/kg) | 6.19 | 6.15 | 7.63 | 7.70 | 7.39 | 7.80 |
| $C_0$ (µg/mL) | 27.7 | 21.2 | 165 | 194 | 263 | 245 |
| CL (mL/h/kg) | 161 | 163 | 131 | 130 | 136 | 128 |
| $V_{ss}$ (L/kg) | 1.24 | 1.08 | 1.53 | 1.14 | 1.41 | 1.29 |
| $T_{1/2}$ (h) | 8.25 | 7.18 | 10.9 | 8.69 | 7.99 | 9.76 |
| Day 13 | | | | | | |
| $AUC_{inf}$ (µg · h/mL) | 21.0 | 16.6 | 329 | 291 | 380 | 387 |
| DN $AUC_{inf}$ (µg · h/mL)/(mg/kg) | 6.76 | 5.37 | 10.7 | 9.45 | 8.20 | 8.35 |
| $C_0$ (µg/mL) | 24.0 | 4.76 | 202 | 105 | 269 | 240 |
| CL (mL/h/kg) | 148 | 186 | 93.6 | 106 | 122 | 120 |
| $V_{ss}$ (L/kg) | 1.50 | 1.70 | 1.15 | 0.773 | 1.12 | 0.806 |
| $T_{1/2}$ (h) | 9.67 | 8.43 | 10.4 | 6.06 | 7.35 | 5.76 |
| Accumulation Ratio | 1.09 | 0.874 | 1.40 | 1.23 | 1.11 | 1.07 |

In addition, male and female dogs also received a once-weekly IV dose of pafolacianine (3.1, 30.8 and 46.3 mg/kg) for 14 days. Overall, drug concentrations increased with ascending dose, noting that the mean profiles at the two highest dose levels were overlapping. Systemic exposure (AUClast) to pafolacianine was approximately dose-proportional over the range of doses administered (0.9 to 13.9 mg/kg) and within the observed variability (Table 5). There were no apparent or consistent gender differences, and no accumulation or changes in TK were evident after repeated once-weekly dosing for 3 weeks. On both Day 0 and Day 13, CL was slow (relative to hepatic blood flow) and Vss was moderate. Mean T1/2 ranged from approximately 13 to 18 hours.

TABLE 5

| | 0.9 mg/kg | | 9.3 mg/kg | | 13.9 mg/kg | |
|---|---|---|---|---|---|---|
| Parameter | M | F | M | F | M | F |
| Day 0 | | | | | | |
| $AUC_{last}$ (µg · h/mL) | 4.74 (0.531) | 8.40 (4.60) | 58.0 (3.56) | 50.8 (11.3) | 78.5 (10.7) | 79.8 (9.66) |
| DN $AUC_{last}$ (µg · h/ml) (mg/kg) | 5.27 (0.589) | 9.34 (5.11) | 6.24 (0.383) | 5.46 (1.21) | 5.65 (0.771) | 5.74 (0.695) |
| $AUC_{inf}$ (µg · h/mL) | 6.40 (0.961) | 10.5 (4.43) | 81.2 (5.64) | 69.3 (15.9) | 110 (14.1) | 109 (11.6) |
| $C_0$ (µg/mL) | 4.66 (0.887) | 4.75 (1.63) | 62.1 (7.30) | 54.9 (9.81) | 81.8 (17.2) | 79.6 (6.14) |
| CL (mL/min/kg) | 2.39 (0.363) | 1.59 (0.489) | 1.92 (0.126) | 2.35 (0.658) | 2.13 (0.305) | 2.15 (0.224) |
| $V_{ss}$ (L/kg) | 2.31 (0.179) | 1.47 (0.744) | 2.10 (0.161) | 2.38 (0.576) | 2.35 (0.535) | 2.20 (0.511) |
| $T_{1/2}$ (h) | 14.8 (1.93) | 15.0 (1.24) | 16.4 (0.693) | 15.2 (1.87) | 16.2 (3.30) | 15.3 (3.47) |

TABLE 5-continued

| | 0.9 mg/kg | | 9.3 mg/kg | | 13.9 mg/kg | |
|---|---|---|---|---|---|---|
| Parameter | M | F | M | F | M | F |
| Day 13 | | | | | | |
| $AUC_{last}$ (µg · h/mL) | 5.07 (0.643) | 6.63 (0.829) | 65.4 (3.70) | 57.7 (11.2) | 85.9 (9.19) | 94.7 (7.33) |
| DN $AUC_{last}$ (µg · h/ml) (mg/kg) | 5.64 (0.714) | 7.36 (0.921) | 7.03 (0.398) | 6.21 (1.20) | 6.18 (0.661) | 6.81 (0.527) |
| $AUC_{inf}$ (µg · h/mL) | 7.36 (1.33) | 8.42 (1.08) | 85.1 (9.61) | 76.6 (16.8) | 117 (12.2) | 129 (8.43) |
| $C_0$ (µg/mL) | 5.73 (1.38) | 8.92 (2.97) | 72.6 (13.5) | 67.8 (13.4) | 108 (12.1) | 104 (15.9) |
| CL (mL/min/kg) | 2.09 (0.373) | 1.80 (0.250) | 1.84 (0.201) | 2.11 (0.547) | 2.00 (0.220) | 1.81 (0.120) |
| $V_{ss}$ (L/kg) | 2.42 (0261) | 1.49 (0.187) | 1.60 (0.175) | 1.94 (0.296) | 2.02 (0.383) | 1.83 (0.287) |
| $T_{1/2}$ (h) | 17.6 (2.57) | 13.1 (0.247) | 13.3 (0.303) | 14.3 (1.22) | 15.0 (3.48) | 15.3 (2.27) |

Overall, in both species, mean CL was found to be slow relative to hepatic blood flow, and mean Vss values were higher that total body water volume, or 668 and 693 mL/kg for rat and monkey, respectively. This suggested distribution of pafolacianine into tissues. There was no observable change in TK with repeat dosing, and PK for both genders was similar.

Distribution

The mean volume of distribution ($V_z$) is 17.1±5.99 L, indicating distribution into tissues.

Plasma protein binding of pafolacianine is 93.7%. No notable partitioning into red blood cells has been observed.

Tissue distribution was evaluated in male and female rats after receiving a single 2 mg/kg (~25 µCi/kg) IV dose of [14C] pafolacianine. Radioactivity levels (pafolacianine equivalents) in tissues were determined over time using QWBA. Radioactivity was rapidly (within 15 minutes) and widely distributed to most tissues. Tissue to plasma ratios for radioactivity were >1.0 for all tissues in male and female animals, with the exception of bone (femur), brain, eye and fat, indicating distribution of [14C] pafolacianine-derived radioactivity to tissues. The overall highest concentration of radioactivity at 24 hours post-dose was measured in the kidneys of male and female rats. There was approximately 11% of the dose remaining in the kidneys at 96 hr post dose. The lowest concentrations of radioactivity were found in the brain and eye. [14C] pafolacianine-derived radioactivity concentrations in the eye, uveal tract and skin of male pigmented (Long Evans) rats were generally similar to those found in albino Sprague Dawley rats, suggesting that there was no affinity of [14C] pafolacianine-derived radioactivity for melanin-containing tissues.

Plasma Protein Binding

The plasma protein binding of pafolacianine was studied in vitro in fresh human, Sprague Dawley rat, and Beagle dog plasma using equilibrium dialysis. Pafolacianine was introduced into plasma samples, in duplicate, resulting in a final concentration of 5 µM. The mean (±SD) percentage of plasma protein bound pafolacianine was 99.1±0.1%, 98.6±0.1%, and 93.7±1.5% for rat, dog and human, respectively. Pafolacianine was highly bound to plasma protein in all species examined.

PK Parameters in Humans

A total of 73 potentially eligible healthy volunteers gave written acknowledgement of informed consent to participate in a Phase 1a study to assess the safety and pharmacokinetics of pafolacianine versus placebo. Fifty-four were found suitable for participation, of which 30 were enrolled in the study. Twenty-four subjects were white, 1 subject was Black/African-American, 1 was Asian, 1 was mixed race and 3 were of another race. Table 6 shows the characteristics of the study population.

TABLE 6

| Characteristics | Pafolacianine (N = 23) | Placebo (N = 7) |
|---|---|---|
| Age in yrs. mean (range) | 30.3 (18-64) | 20 (20-29) |
| Males (n, %) | 10 (43) | 2 (29) |
| BMI (kg/m$^2$) | 23.7 | 21.4 |

The pharmacokinetic (PK) analysis population was defined as all subjects who were randomized and received study treatment. Of note, the drug infusion was stopped prematurely in 1 subject, and interrupted in another subject. The pharmacokinetics of pafolacianine following single IV administration of 0.025, 0.05, 0.1, or 0.2 mg/kg was determined using non-compartmental analysis; the key PK parameters are summarized in Table 7.

TABLE 7

| Parameter | Mean (SD) | | | | | |
|---|---|---|---|---|---|---|
| Pafolacianine Dosage (mg/kg) | 0.025 | 0.05$^b$ | 0.1$^b$ | | 0.2$^b$ | |
| $C_{max}$ (ng/mL) | 93.3 (49.2)$^a$ | 59.1 (5.9)$^b$ | 184 (32.2) | 450 (45.7) | 640 (115) | 765 (120)$^c$ |
| $T_{max}$ (hr) | 0.75 (0.43)$^a$ | 0.95 (0.14)$^b$ | 1.03 (0.02) | 1.02 (0.01) | 1.09 (0.11) | 1.00 (0)$^c$ |
| $AUC_{0\text{-}last}$ (ng*hr/mL) | 63.4 (10.1)$^a$ | 61.6 (12.4)$^b$ | 250 (53.7) | 785 (157) | 1310 (178) | 1400 (194)$^c$ |
| $T_{1/2}$ (hr) | 0.416 (0.063)$^a$ | 0.438 (0.229)$^b$ | 0.931 (0.207) | 1.64 (0.22) | 2.66 (0.41) | 2.40 (0.48)$^c$ |
| $AUC_{0\text{-}inf}$ (ng*hr/mL) | 66.4 (10.1)$^a$ | 63.6 (12.6)$^b$ | 258 (54.8) | 799 (162) | 1340 (180) | 1430 (183)$^c$ |
| CL (L/hr) | 26.6 (3.1)$^a$ | 28.6 (5.0)$^b$ | 14.7 (3.33) | 9.67 (4.07) | 10.0 (0.97) | 10.2 (1.7)$^c$ |
| $V_z$ (L) | 15.9 (1.3)$^a$ | 17.1 (6.0)$^b$ | 19.2 (3.7) | 22.2 (6.6) | 38.8 (9.2) | 36.0 (13.3)$^c$ |

$^a$OTL38 dissolved in 20 ml 0.9% NaCl over 10- and 60-min infusion
$^b$OTL38 dissolved in 220 ml of 5% dextrose solution over 60-min infusion
$^c$OTL38 with pre-treatment of anthistamine (clemastine)

The maximal concentration for each dose (Cmax) was obtained near the end of infusion. After completion of the infusion, plasma concentrations declined rapidly. The drug concentration-time profiles obtained at the higher doses suggest that the decline in plasma concentration is (at least) bi-phasic. Exposure (as measured by Cmax and AUClast) increased as the dose of pafolacianine was escalated. As the dose escalated 8-fold (0.025 to 0.2 mg/kg) Cmax values increased ~12-fold whereas AUClast values rose ~22-fold, suggesting that the increase in exposure with dose was greater than dose proportional. Clearance values (CL) decreased with dose, indicating that clearance may be saturable at higher doses, which is consistent with the greater than dose proportional increase in exposure. Overall, the clearance was moderate to low relative to hepatic blood flow (~84 L/hr for a 70 kg subject) and varied from ~29 to 10 L/hr over the dose range. Drug half-life values were short and ranged from ~0.4 to 2.7 hr.

Example 7: Safety Evaluation of Compositions Including Pafolacianine

The safety of the disclosed compositions were evaluated in three open label clinical studies, two studies (N=150 and N=44) in patients with ovarian cancer and one study (N=100) in patients with cancer in the lung. A total of 294 patients received 0.025 mg/kg of the disclosed compositions via intravenous administration. The mean age of patients was 63.5 years; 51% were 65 years of age or older; 89% of patients were female; and 84% of patients were white.

Adverse reactions that occurred in >1% of patients were: nausea (15%), vomiting (5.8%), abdominal pain (2.7%), flushing (1.7%), dyspepsia (1%), chest discomfort (1%), pruritus (1%) and hypersensitivity (1%). In 2.4% of patients, these adverse reactions occurred during the administration of the composition. Reactions typically occurred within 15 minutes of the start of infusion.

Example 8: Ex Vivo Evaluation of Sensitivity and Specificity of Cameras Using Pafolacianine Pafolacianine sodium (2 mg/mL in 1.6 mL of PBS, 1414.2 g/mol (or Da), λex=774-776 nm, λem=794-796 nm) was serially diluted by 100 folds from 100 μM to 1 pM using PBS or 5% dextrose solution. The diluent was used as a negative control and ICG (10 uM with the same diluent) will be used as a positive control. The serially diluted samples were transferred into 96 black-well plates and imaged with the camera under evaluation to determine the sensitivity of the camera.

Depth Penetration

Fresh porcine flesh was purchased from the Butcher Block and cut into slabs of 1 cm thickness. 100 μL solution of 10 μM pafolacianine sodium was dispensed into glass tubes and placed under the porcine flesh. Images were taken using the camera under evaluation. The number of porcine flesh slabs were increased and imaged to determine the depth penetration of the camera.

Preliminary phantom studies were conducted using agarose-based gel phantom constructing agar phantoms having the geometry of desired organ. Sizes ranging from 3 mm to 10 mm glass tubes with 10 μM of pafolacianine sodium (100 μL) were placed in the agar phantom gel at various measured distances and imaged to determine the depth penetration of the camera.

Field of View

100 μL solution of 10 μM pafolacianine sodium was dispensed into 9 glass tubes and placed in the center and on the 8 arrows as shown in FIG. 5. Images were taken using the camera under evaluation to determine uniform field of view.

Example 9: In Vivo Evaluation of Sensitivity and Specificity of Cameras Using Pafolacianine KB cells (a derivative of HeLa/human cervical cancer cell line that expresses ~2×10$^6$ folate receptors/cell) and A549 cells (a alveolar basal epithelial carcinoma cell line that do not express folate receptor) were obtained from ATCC (Rockville, MD) and grown as a monolayer using folate free or normal 1640 RPMI-1640 medium (Gibco, NY) containing 10% heat-inactivated fetal bovine serum (Atlanta Biological, GA) and 1% penicillin streptomycin (Gibco, NY) in a 5% carbon dioxide:95% air-humidified atmosphere at 37° C. for at least six passages before they were used for the studies.

Athymic female nude (nu/nu) mice (5 to 6 weeks old, 18-20 g) were purchased from Envigo (Indianapolis, IN) and maintained on gamma-irradiated folate-deficient special diet (Envigo, IN) for 2 weeks before the start of the study. Animals were housed 5 per cage in a barrier, pathogen-free cloaked rack. Autoclaved tap water and food will be given as needed. The animals were housed in a sterile environment on a standard 12 h light-dark cycle for the duration of the study.

Seven-week-old female nu/nu mice were inoculated subcutaneously with $1.0 \times 10^6$ KB cell or A549 cells/mouse in RPMI1640 medium on the shoulder or neck. The A549 xenografts model was used as negative control to determine the receptor specificity of pafolacianine sodium. Growth of the tumors were measured in perpendicular directions every 2 days using a caliper (body weights were monitored on the same schedule), and the volumes of the tumors were calculated as $0.5 \times L \times W^2$ (L=longest axis and W=axis perpendicular to L in millimeters). Once tumors reached approximately 300-400 mm$^3$ in volume, animals (5 mice/group) were intravenously injected with an appropriate dose of pafolacianine sodium (2-4 nmol, i.e., HDE of 0.0125-0.025 mg/kg) in PBS or 5% dextrose solution. For whole body imaging and biodistribution studies, animals were euthanized after 2 to 3 h of administration of pafolacianine sodium by $CO_2$ asphyxiation. For time dependent studies, animals were imaged under anesthesia using isoflurane. Following whole body imaging, animals were dissected and selected tissues were analyzed for fluorescence activity using camera of interest and the ROIs of the tissues were calculated using appropriate software.

Tumors were further dissected into small pieces (e.g., ½, ¼, ⅛, 1/16, etc.) and imaged either directly or surgically placing in an organ of interested (e.g., lung, liver, kidney, etc.) in a large animal such as pig, dog, human cadaver, or another animal to determine the camera sensitivity (i.e., to see the ability of the camera in determining the smallest tumors with the appropriate environment).

Example 10: Embryo-Fetal Development (EFD) Animal Studies

Pafolacianine was intravenously administered at doses of, during the period of organogenesis namely, 0.015, 0.15, and 1.5 mg/kg/day from gestational day (GD) 6 to GD17 in rats (human equivalent doses (HEDs) of 0.002, 0.024 and 0.242 mg/kg/day) and 0.3, 1, and 3 mg/kg/day from GD7 to GD20 in rabbits (HEDs of 0.097, 0.323 and 0.968 mg/kg/day). No significant drug-related maternal toxicity and embryo-fetal development toxicity were observed. No-Observed-Adverse-Effect-Levels were 1.5 mg/kg/day in rats and 3 mg/kg/day in rabbits. Estimated systemic exposures were 158 times (rat) and 570 times (rabbit) the human exposure at a human dose of 0.025 mg pafolacianine per 1 kg bodyweight of the patient based on area under the plasma concentration-time curve (AUC) comparison.

While the present disclosure has been described with reference to certain embodiments, it will be understood by those skilled in the art that various changes may be made and equivalents may be substituted without departing from the scope of the present disclosure or appended claims. In addition, many modifications may be made to adapt a particular situation or material to the teachings of the present disclosure without departing from its scope. Therefore, it is intended that the present disclosure not be limited to the particular embodiments disclosed, but that the present disclosure will include all aspects falling within the scope of the appended claims.

All patents, patent applications, publications, and descriptions mentioned above are herein incorporated by reference in their entirety.

The invention claimed is:

1. A composition to be administered to a subject undergoing a malignant lesion resection procedure, the composition comprising a pharmaceutically effective amount between about 1 mg and about 20 mg of pafolacianine or pharmaceutically acceptable salt thereof, per about 1.6 mL volume of solution; about 3.2 mg pafolacianine or pharmaceutically acceptable salt thereof; about 14.4 mg sodium chloride; about 0.23 mg potassium phosphate monobasic; and about 1.27 mg sodium phosphate dibasic heptahydrate; and wherein the composition has a pH between about 7.1 to 7.8; wherein the pafolacianine or pharmaceutically acceptable salt thereof binds to at least one malignant lesion and emit an optical signal.

2. The composition of claim 1, wherein the at least one malignant lesion is an ovarian cancer malignant lesion or a lung cancer malignant lesion.

3. The composition of claim 1, wherein the administration is intravenous.

4. The composition of claim 1, wherein the pharmaceutically acceptable salt of pafolacianine has the following chemical structure:

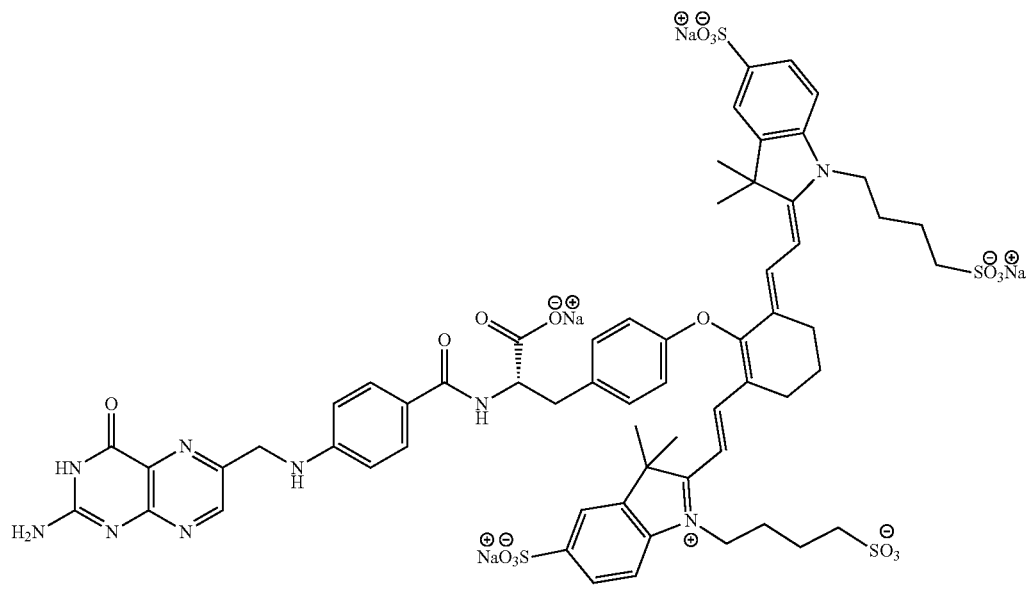

5. The composition of claim 1, wherein the composition is administered to the subject about 1 to about 24 hours prior to the malignant lesion resection procedure.

6. The composition of claim 1, wherein the pafolacianine or pharmaceutically acceptable salt thereof fluoresces upon exposure to light in the near-infrared range.

7. A method of treating a subject undergoing a malignant lesion resection procedure, the method comprising:
administering a pharmaceutically effective amount of a composition comprising between about 1 mg and about 20 mg of pafolacianine or pharmaceutically acceptable salt, per about 1.6 mL volume of solution, about 3.2 mg pafolacianine or pharmaceutically acceptable salt thereof; about 14.4 mg sodium chloride; about 0.23 mg potassium phosphate monobasic; and about 1.27 mg sodium phosphate dibasic heptahydrate; and wherein the composition has a pH between about 7.1 to 7.8; wherein the pafolacianine or pharmaceutically acceptable salt thereof distributes in a least of portion of one or more malignant lesions;
illuminating the one or more malignant lesions with an excitation light of a wavelength absorbable by the pafolacianine or pharmaceutically acceptable salt thereof;
and detecting the optical signals emitted by the pafolacianine or pharmaceutically acceptable salt thereof.

8. The method of claim 7, further comprising identifying, based on the optical signals emitted, the one or more malignant lesions.

9. The method of claim 7, further comprising resecting the one or more of the malignant lesions.

10. The method of claim 9, wherein the resection procedure is non-invasive, is performed manually or using robotic-assisted technology, and/or performed using iBiopsy, iKnife, iLaser, iBurner, an electric cutting loop, a rotating blade, a curved blade, an expandable blade, dissectors with cutting blades, blunt dissectors, pinchers, an electrical cutting element, a biopsy needle, microwave ablation probe, radiofrequency ablation probe, cryo-ablation probe, or laser.

11. The method of claim 7, wherein the one or more malignant lesions is an ovarian cancer malignant lesion or a lung cancer malignant lesion.

12. The method of claim 7, wherein the optical signal is detected using an imaging system or imaging software.

13. The method of claim 12, wherein the imaging system or imaging software is selected from the group consisting of imaging system FAST (fiber-optic array scanning technology), flow cytometry, confocal microscopy, two-photon microscopy, epifluorescence microscopic, florescence microscopic methods, and fluorescence goggles.

14. The method of claim 7, wherein the method further comprises guiding a flexible probe to the at least one malignant lesion after administration of the composition.

15. The method of claim 13, wherein the flexible probe is a flexible endoscope, fluorescence endoscopic imaging probe, fiber scope, video scope, gastroscope, colonoscope, bronchoscope, laryngoscope, cystoscope, duodenoscope, enteroscope, ureteroscope, sigmoidoscope, enteroscope, choleodo scope, rhinolaryngo scope, angioscope, or hysteroscope.

* * * * *

UNITED STATES PATENT AND TRADEMARK OFFICE
CERTIFICATE OF CORRECTION

PATENT NO. : 11,986,540 B2
APPLICATION NO. : 18/111704
DATED : May 21, 2024
INVENTOR(S) : Sumith A. Kularatne Page 1 of 1

It is certified that error appears in the above-identified patent and that said Letters Patent is hereby corrected as shown below:

In the Claims

Column 22, Lines 38-55 Claim 1 should read:
1. A composition to be administered to a subject undergoing a malignant lesion resection procedure, the composition comprising about 3.2 mg pafolacianine or pharmaceutically acceptable salt thereof; about 14.4 mg sodium chloride; about 0.23 mg potassium phosphate monobasic; and about 1.27 mg sodium phosphate dibasic heptahydrate; and wherein the composition has a pH between about 7.1 to 7.8; wherein the pafolacianine or pharmaceutically acceptable salt thereof binds to at least one malignant lesion and emits an optical signal.

Column 23, Lines 32-51 Claim 7 should read:
7. A method of treating a subject undergoing a malignant lesion resection procedure, the method comprising:
administering about 3.2 mg pafolacianine or pharmaceutically acceptable salt thereof; about 14.4 mg sodium chloride; about 0.23 mg potassium phosphate monobasic; and about 1.27 mg sodium phosphate dibasic heptahydrate; and wherein the composition has a pH between about 7.1 to 7.8; wherein the pafolacianine or pharmaceutically acceptable salt thereof distributes in a least of portion of one or more malignant lesions;
illuminating the one or more malignant lesions with an excitation light of a wavelength absorbable by the pafolacianine or pharmaceutically acceptable salt thereof;
and detecting the optical signals emitted by the pafolacianine or pharmaceutically acceptable salt thereof.

Signed and Sealed this
Twenty-fourth Day of September, 2024

Katherine Kelly Vidal
*Director of the United States Patent and Trademark Office*